US010849604B2

(12) United States Patent
Yang

(10) Patent No.: US 10,849,604 B2
(45) Date of Patent: Dec. 1, 2020

(54) METHOD OF REMOVING AN APPENDIX

(71) Applicant: GYRUS MEDICAL LIMITED, Cardiff (GB)

(72) Inventor: Teo Heng Jimmy Yang, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 193 days.

(21) Appl. No.: 16/241,267

(22) Filed: Jan. 7, 2019

(65) Prior Publication Data

US 2019/0209148 A1 Jul. 11, 2019

Related U.S. Application Data

(60) Provisional application No. 62/614,008, filed on Jan. 5, 2018.

(51) Int. Cl.
*A61B 17/00* (2006.01)
*A61B 17/12* (2006.01)
(Continued)

(52) U.S. Cl.
CPC ........ *A61B 17/00234* (2013.01); *A61B 17/29* (2013.01); *A61B 17/3474* (2013.01);
(Continued)

(58) Field of Classification Search
CPC .... A61B 2017/0488; A61B 2017/1125; A61B 2017/1225; A61B 2017/00278;
(Continued)

(56) References Cited

U.S. PATENT DOCUMENTS 5,630,822 A * 5/1997 Hermann ......... A61B 17/00234
606/114
6,383,195 B1 * 5/2002 Richard ............... A61B 17/221
606/114
(Continued)

OTHER PUBLICATIONS

T.N. Pappas et al., Atlas of Laparoscopic Appendectomy, Chapter 16, Laparoscopic Appendectomy, Springer Science, pp. 16.2-16.15. (Year: 1996).*

*Primary Examiner* — Ashley L Fishback
*Assistant Examiner* — Uyen N Vo
(74) *Attorney, Agent, or Firm* — Oliff PLC

(57) ABSTRACT

A method of removing an appendix (9) includes the steps of accessing the abdomen of a patient, insufflating the abdominal cavity, and sealing and cutting the appendicular artery and vein. A sheath is introduced into the abdominal cavity and placed over the appendix, while the appendix is still attached to the colon. The sheath is secured the sheath in place over the appendix using a securing device to secure the sheath with respect to the proximal end of the appendix, and then the proximal end of the appendix is ligated. The appendix is dissected from the colon, and the sheath containing the appendix is removed from the abdomen of the patient. The procedure can be a NOTES procedure, using a natural orifice, or laparoscopic using one or more incisions created in the abdomen. The ligation and dissection can be performed within the abdomen, or after the appendix is pulled through one of the incisions, such that the ligation and/or dissection is carried out outside the abdomen.

20 Claims, 7 Drawing Sheets

(51) Int. Cl.
*A61B 17/122* (2006.01)
*A61B 17/34* (2006.01)
*A61B 17/29* (2006.01)
*A61B 17/04* (2006.01)
*A61B 17/11* (2006.01)

(52) U.S. Cl.
CPC ....... *A61B 17/0487* (2013.01); *A61B 17/1114* (2013.01); *A61B 17/122* (2013.01); *A61B 17/12013* (2013.01); *A61B 2017/00278* (2013.01); *A61B 2017/00287* (2013.01); *A61B 2017/00637* (2013.01); *A61B 2017/00823* (2013.01)

(58) Field of Classification Search
CPC .. A61B 2017/00287; A61B 2017/0637; A61B 2017/00823; A61B 2017/00292; A61B 17/00234; A61B 17/0218; A61B 17/0469; A61B 17/12013; A61B 17/1285; A61B 17/320016; A61B 17/29; A61B 17/3474; A61B 17/0487; A61B 17/1114; A61B 17/142; A61B 17/122

USPC ....................................................... 606/205
See application file for complete search history.

(56) References Cited

U.S. PATENT DOCUMENTS

| | | | |
|---|---|---|---|
| 6,752,822 B2* | 6/2004 | Jespersen | A61B 17/00234 606/114 |
| 2005/0222576 A1* | 10/2005 | Kick | A61B 17/3439 606/104 |
| 2006/0058776 A1* | 3/2006 | Bilsbury | A61B 17/221 604/540 |
| 2010/0076451 A1* | 3/2010 | Zwolinski | A61B 1/005 606/113 |
| 2011/0112434 A1* | 5/2011 | Ghabrial | A61B 17/3423 600/564 |
| 2014/0052018 A1* | 2/2014 | Hawkins | A61B 1/3132 600/562 |
| 2016/0324515 A1* | 11/2016 | Ravikunnar | A61B 17/221 |

* cited by examiner

METHOD OF REMOVING AN APPENDIX

This invention relates to a method for removing an appendix. Appendectomy has traditionally been performed as an open procedure with a large incision and direct access to the abdomen. More recently, laparoscopic appendectomy has sometimes been performed, with multiple access ports in the patient's abdomen. In this procedure, the appendix is dissected and placed into a tissue bag within the patient, and then removed through one of the ports. However, there is always the risk that the appendix may burst during the procedure, or that the contents of the cecum can leak during the procedure.

The present invention provides a method of removing an appendix in which these risks are reduced or eliminated. Accordingly, a method of removing an appendix comprises the steps of:

a) accessing the abdomen of a patient,
b) insufflating the abdominal cavity,
c) sealing the appendicular artery and vein,
d) cutting the appendicular artery and vein (along with any supporting tissue),
e) introducing a sheath into the abdominal cavity and placing it over the appendix, while the appendix is still attached to the colon, and then, in any order, f) ligating the proximal end of the appendix,
g) dissecting the appendix from the colon, and
h) removing the sheath containing the appendix through one of the incisions in the abdomen of the patient.

The sheath may be placed over the appendix in place before the appendix is dissected or removed. This means that should the appendix burst during dissection or removal, or should matter leak during this time, the matter is contained within the sheath. The sheath may be placed over the appendix using an applicator, which is introduced into the patient and is capable of deploying the sheath so that it can be placed over the appendix. The sheath is conveniently held in place by a securing device, which is conceivably a clip applied to the sheath over the proximal end of the appendix (mesoappendix). Alternatively, the sheath is conceivably provided with draw strings, which can be tightened to close the sheath over the mesoappendix. It is to be appreciated that a tissue bag may be used as an alternative to a sheath provided it is suitable to carry out the aforementioned function of containing the appendix within the abdominal cavity prior to dissection or removal and retention of any leaked matter during the appendectomy procedure.

Once the sheath is covering the appendix, the appendix can be ligated in order to isolate it. By the terms "ligated" or "ligating", there is herein meant to include any means of isolating the appendix such that it is sealed from surrounding tissue, including the use of clips, staples, or sutures applied to the appendix. Once the appendix is ligated, it can be dissected from surrounding tissue and removed from the patient. This can be done in various ways, as follows. According to a first arrangement, the appendix is firstly ligated in step f) within the patient, the appendix is secondly dissected in step g) within the patient, and the sheath is thirdly removed containing the dissected appendix in step h). In this method, the isolation and dissection of the appendix is performed within the abdomen, and the dissected appendix then removed from the patient.

The abdomen of the patient is conceivably accessed by the introduction of one or more instruments via a natural orifice of the patient. This type of procedure is generally known as a NOTES procedure. Alternatively, the abdomen of the patient is conceivably accessed by the creation of one or more incisions therein, and the introduction of one or more instruments through the incisions. This is a more typical Laparoscopic procedure.

According to an alternative arrangement used in a laparoscopic procedure, the appendix is firstly ligated in step f) within the patient, the sheath containing the undissected appendix is secondly removed through one of the incisions in step h), and the appendix is thirdly dissected in step g) outside the patient. In this method, the isolation of the appendix is performed within the abdomen, and the undissected appendix is pulled through the incision in order to be dissected outside the patient. The insufflation of the abdomen may need to be reduced in order to bring the appendix adjacent the incision.

According to a further laparoscopic arrangement, the sheath containing the undissected appendix is firstly removed through one of the incisions in step h), the appendix is secondly ligated outside the patient in step f), and the appendix is thirdly dissected in step g) outside the patient. In this method, the undissected appendix is pulled through an incision in order to be isolated and dissected outside the patient. Once again, the insufflation of the abdomen may need to be reduced in order to bring the appendix adjacent the incision.

Preferably, at least one of the incisions is in the umbilicus. In step h), the sheath containing the appendix is conveniently removed through the umbilicus. The umbilicus provides a pathway sufficient for the appendix to be safely removed, or, where the appendix has not yet been dissected, the appendix can be pulled through the umbilicus to be dissected outside the abdomen.

The invention will now be further described, by way of example only, with reference to the accompanying drawings, in which FIG. 1 is a schematic drawing of the human appendix and the surrounding anatomy;

Figure 1:
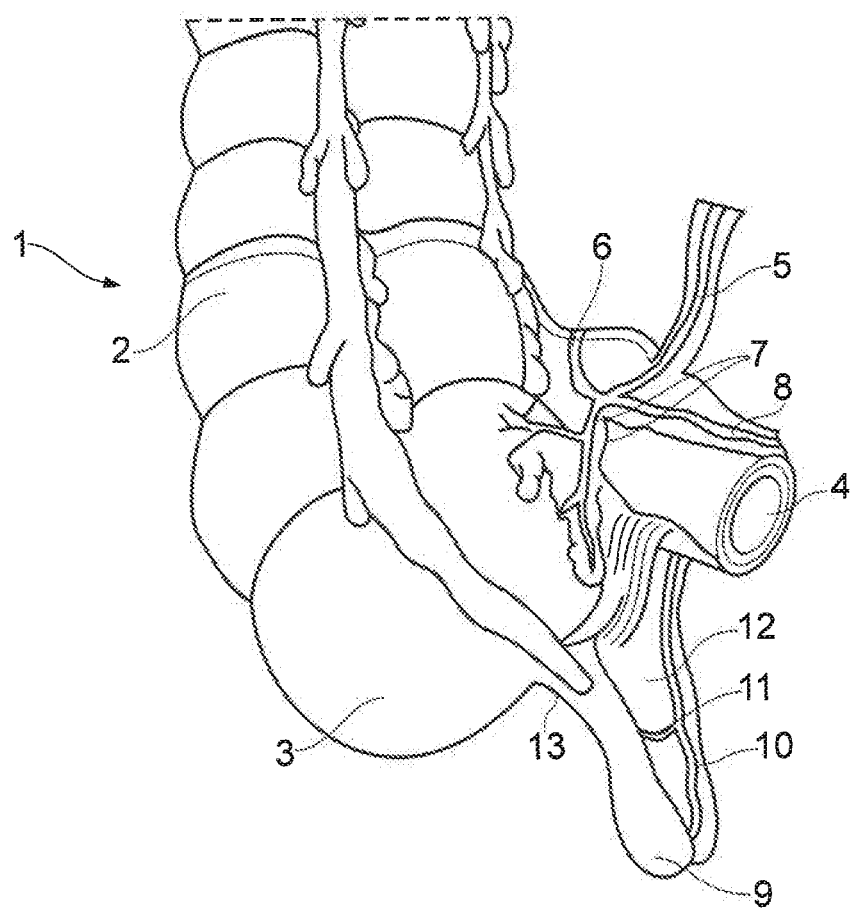
Figure 2:
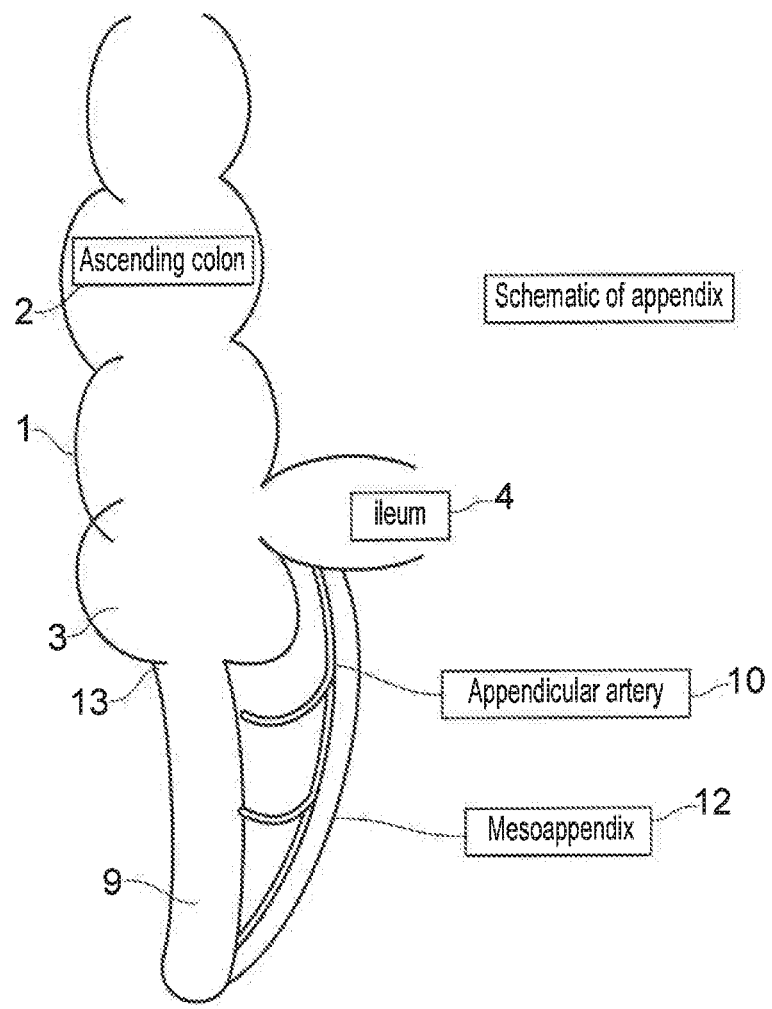
FIG. 2 is an illustration of the human appendix shown in the schematic drawing of FIG. 1.

Referring to FIGS. 1 and 2, the colon is shown generally at 1, and includes the ascending colon 2 and the cecum 3 at the lower part of the colon. The ileum 4 extends from the colon 1 and is supplied with blood by the ileocecal artery 5. The ileocecal artery splits into different branches in the region of the ileum, including the ascending branch 6, the anterior and posterior cecal branches 7, and the ileal branch 8.

The appendix 9 also extends from the colon, and is supplied with blood by the appendicular artery 10 and various veins indicated at 11. The mesoappendix 12 is also attached to the appendix 9, connecting the appendix to the abdominal wall (not shown).

Figure 3:
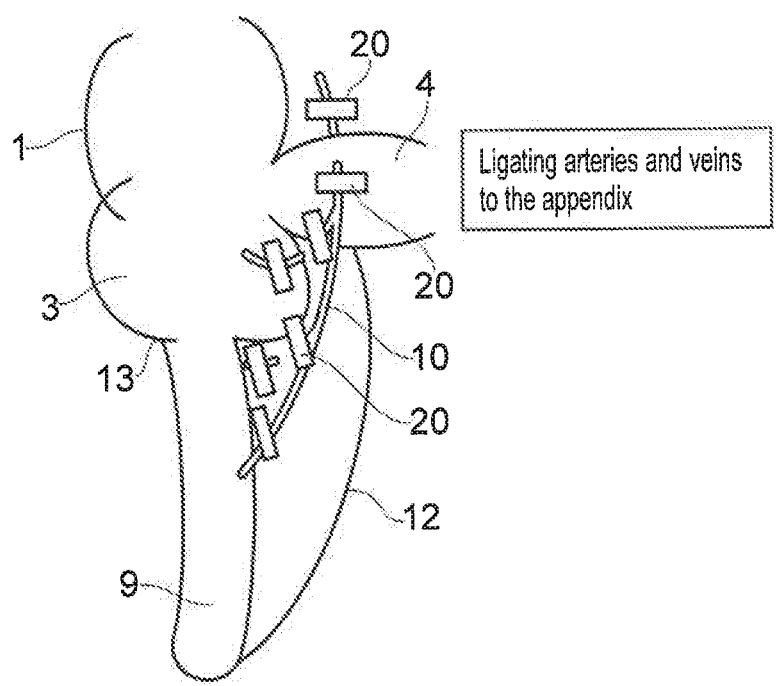
FIG. 3 is an illustration of the appendix of FIG. 2 with ligation clips in place on the arteries and veins.

Various methods of removing the appendix 9 will now be described, starting with the simplest. In this method, one or more incisions are made in the abdomen of the patient, typically one for the insertion of an endoscopic camera, one for insufflation of the abdomen and a third for the insertion of one or more instruments. Fewer incisions can be made if these functions are combined. Typically, at least one of the incisions is made in the umbilicus 24. Once the surgical site is insufflated and visualised, a surgical instrument is used to seal and then cut the appendicular artery 10 and surrounding veins 11 so as to cut off the blood supply to the appendix. FIG. 3 shows the identification of arteries leading to the appendix and veins draining to the ileocolic vein and the presence of suitably located clips or energy seals 20 on the arteries and veins in preparation for ligating the arteries and veins.

Then, a sheath (or tissue bag) 22 is introduced into the surgical site and placed over the appendix. The sheath 22 is secured over the appendix by means of one or more clips, or by means of one or more drawstrings 28 tightened at the proximal end of the appendix 9 (in the region 13 where the appendix 9 meets the cecum 3). In a variation of the procedure, the sheath 22 is secured over the appendix as an initial step, before the sealing and cutting of the appendicular artery 10 and veins 11.

Figure 4:
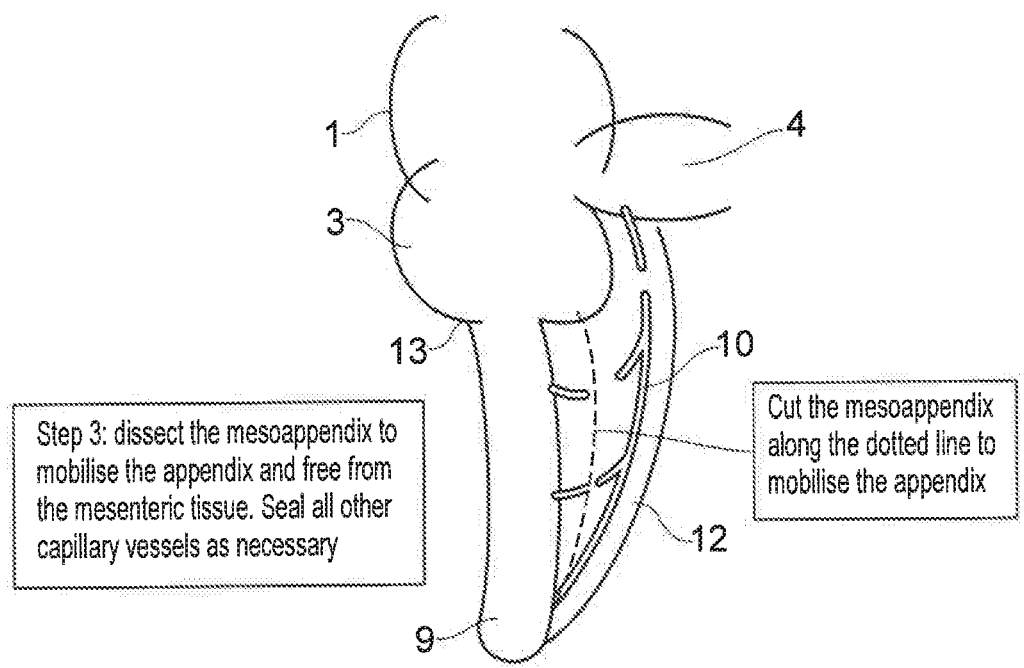
FIG. 4 is an illustration of the appendix of FIG. 2, showing dissection of the appendix from the mesenteric tissue.

Once the sheath 22 is secured over the appendix 9, the appendix is ligated in the region 13 by means of clips, staples or sutures 20, in order to isolate the appendix from the cecum 3. Once isolated, the appendix 9 is dissected from the cecum 3, and the mesoappendix 12 is dissected to separate the appendix from all connecting tissue, as shown in FIG. 4. This mobilises the appendix and frees it from the mesenteric tissue. All other capillary vessels are sealed as necessary to assist with this process. The dotted line of FIG. 4 identifies where the mesoappendix is cut during the mobilisation of the appendix. During this dissection, the sheath 22 ensures that the appendix is contained, such that should it leak or burst any matter is contained within the sheath 22.

Once the appendix 9 is separated from connecting tissue, the sheath 22 containing the separated appendix is removed from the abdomen through one of the incisions, typically through the umbilicus 24. As before, the sheath 22 ensures that the appendix is contained during removal.

In an alternative method, the one or more incisions are made as previously described, the surgical site is insufflated and visualised, and the appendicular artery 10 and surrounding veins 11 are sealed and cut as before. The sheath 22 is introduced into the surgical site and placed over the appendix, again as before. Again, as previously described, the appendix is ligated in the region 13 by means of clips, staples or sutures 20, in order to isolate the appendix from the cecum 3. Where the procedure differs is that the appendix is then pulled through the incision, enclosed within the sheath 22 for protection, and the dissection of the appendix 9 and the mesoappendix 12 takes place outside the abdomen. It is likely that the insufflation of the abdomen will need to be reduced at this point, so that the appendix can be maneuvered adjacent the incision and pulled through for external dissection. As before, the presence of the sheath 22 around the appendix 9 means that any leakage or bursting of the appendix during manipulation or dissection is contained.

Figure 5:
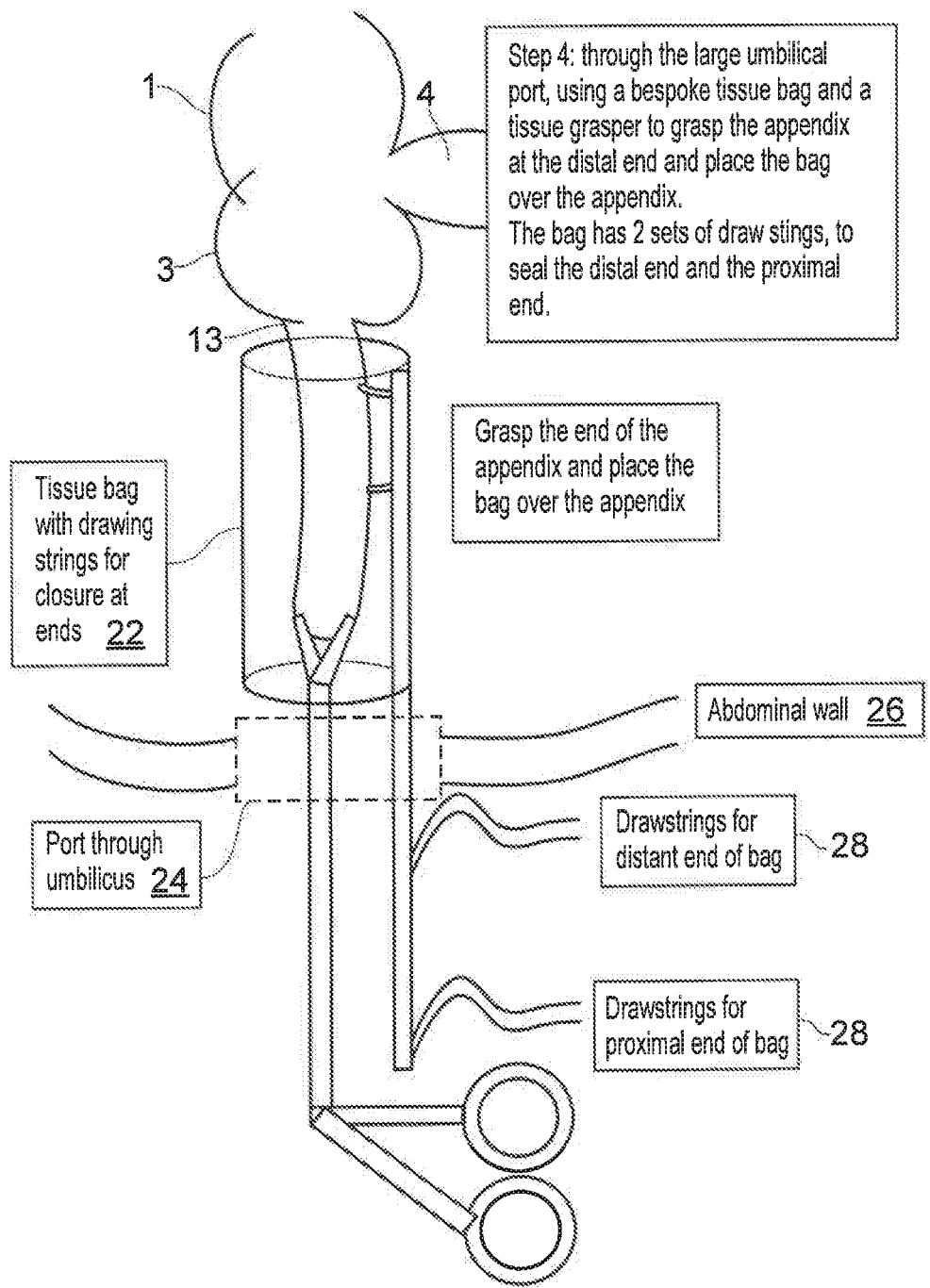
FIG. 5 is an illustration of the appendix of FIG. 2, showing the removal of the dissected appendix within a sheath through the abdominal wall via the umbilicus.
Figure 6:
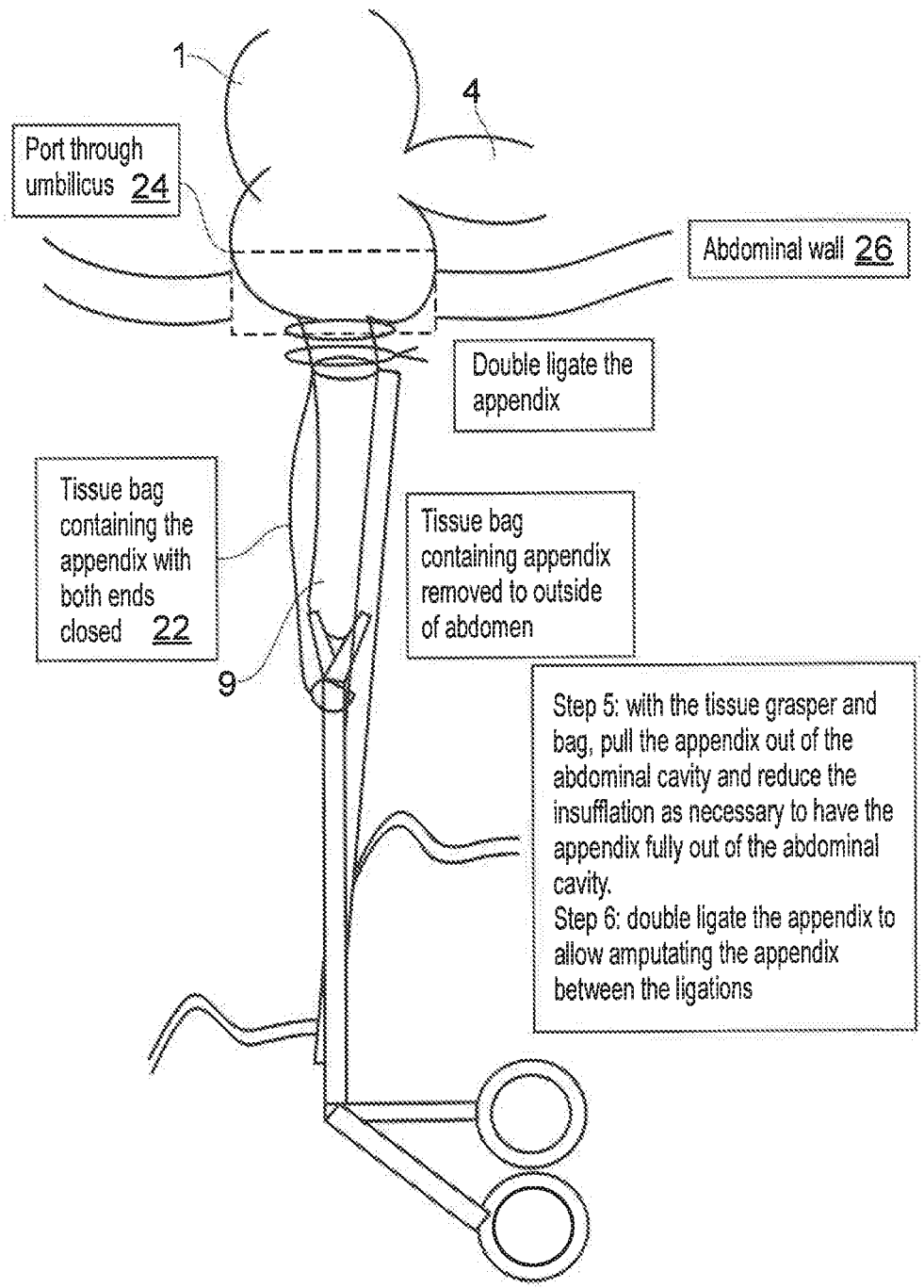
FIG. 6 is an illustration of the appendix of FIG. 2, showing the double ligation of the appendix after removal of the sheathed appendix from the abdominal cavity.
Figure 7:
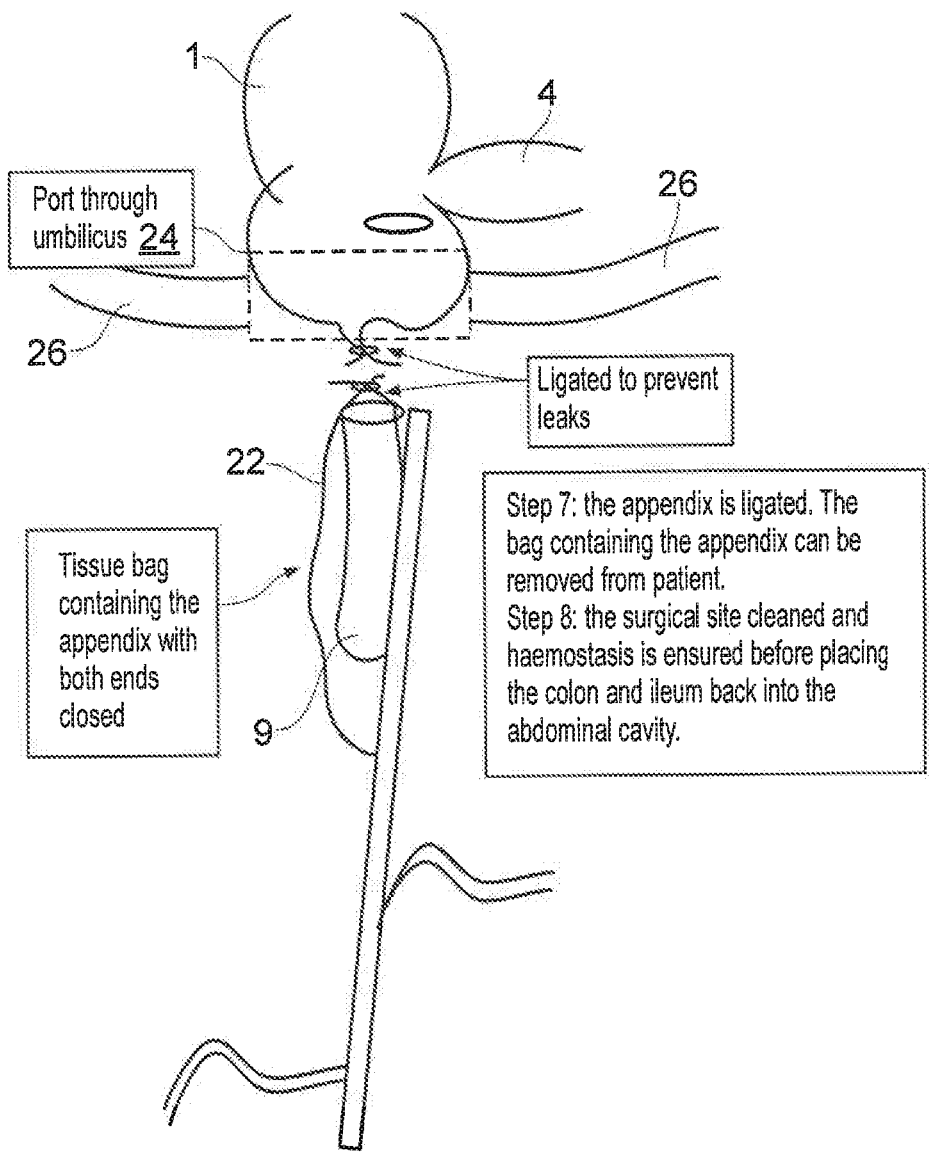
FIG. 7 is an illustration of the appendix of FIG. 2 ligated from the colon and ileum.

A third option for the surgical procedure will now be described with reference to FIGS. 5 to 7. In this third option, the one or more incisions are made as previously described, the surgical site is insufflated and visualised, and the appendicular artery 10 and surrounding veins 11 are sealed and cut, and supporting tissue structures are dissected as before. The sheath 22 is introduced into the surgical site and placed over the appendix, again as shown in FIG. 5. Where this third option differs is that the appendix 9 is then pulled through the incision in the abdominal wall 26, as shown in FIG. 6 whilst remaining enclosed within the sheath 22 for protection, such that both ligation and dissection of the appendix take place outside of the abdomen. When the appendix is pulled through the incision in abdominal wall 26, it is double ligated, as shown in FIG. 6, in the region 13 by means of clips, staples or sutures 20, in order to isolate the appendix from the cecum 3. The appendix 9 and the mesoappendix 12 is then dissected, also outside the abdomen, as shown in FIG. 7. As before, it is likely that the insufflation of the abdomen will need to be reduced, so that the appendix can be manoeuvred adjacent the incision and pulled through for external ligation and dissection. Also, as before, the presence of the sheath 22 around the appendix 9 means that any leakage or bursting of the appendix during the procedure is contained.

The invention claimed is:
1. A method of removing an appendix of a patient comprising the steps of:
   a) accessing an abdomen of the patient,
   b) insufflating an abdominal cavity,
   c) sealing an appendicular artery and vein of the patient,
   d) cutting the appendicular artery and vein,
   e) introducing a sheath into the abdominal cavity and placing the sheath over an appendix while the appendix is still attached to a colon,
   and then, in any order,
   f) ligating a proximal end of the appendix,
   g) dissecting the appendix from the colon, and
   h) removing the sheath containing the appendix from the abdomen of the patient.

2. A method according to claim 1, wherein the appendix is firstly ligated in step f) within the patient, the appendix is secondly dissected in step g) within the patient, and the sheath is thirdly removed containing the dissected appendix in step h).

3. A method according to claim 1, wherein ligation and dissection of the appendix of steps f) and g) takes place after removal of the sheath containing the appendix from the abdomen of the patient in step h) whilst still attached to the colon.

4. A method according to claim 1, wherein step f) comprises double ligation of the proximal end of the appendix to create a secured section of dissection.

5. A method according to claim 1, wherein the step of introducing the sheath into the abdominal cavity is performed using an applicator capable of being introduced into the patient and deploying the sheath once within the abdominal cavity.

6. A method according to claim 1, wherein the method includes an additional step of securing the sheath in place over the appendix using a securing device to secure the sheath with respect to the proximal end of the appendix.

7. A method according to claim 6, wherein the additional step of securing the sheath in place over the appendix is performed by applying a clip over the sheath securing the sheath to the proximal end of the appendix.

8. A method according to claim 6, wherein the additional step of securing the sheath in place over the appendix is performed by closing one or more drawstrings present on the sheath.

9. A method according to claim 1, wherein the abdomen of the patient is accessed by an introduction of one or more instruments via a natural orifice in a NOTES procedure.

10. A method according to claim 1, wherein the abdomen of the patient is accessed by creation of one or more incisions therein, and the introduction of one or more instruments through the one or more incisions.

11. A method according to claim 10, wherein the appendix is firstly ligated in step f) within the patient, the sheath containing the undissected appendix is secondly removed through the one or more incisions in step h), and the appendix is thirdly dissected in step g) outside the patient.

12. A method according to claim 10, wherein the sheath containing the undissected appendix is firstly removed through the one or more incisions in step h), the appendix is secondly ligated outside the patient in step f), and the appendix is thirdly dissected in step g) outside the patient.

13. A method according to claim 11, wherein the insufflation of step b) is reduced before the undissected appendix is removed through the one or more incisions in step h).

14. A method according to claim 10, wherein at least a first of the one or more incisions is in the umbilicus.

15. A method according to claim 14, wherein in step h) the sheath containing the appendix is removed through the umbilicus.

16. A method according to claim 2, wherein step f) comprises double ligation of the proximal end of the appendix to create a secured section of dissection.

17. A method according to claim 3, wherein step f) comprises double ligation of the proximal end of the appendix to create a secured section of dissection.

18. A method according to claim 2, wherein the step of introducing the sheath into the abdominal cavity is performed using an applicator capable of being introduced into the patient and deploying the sheath once within the abdominal cavity.

19. A method according to claim 3, wherein the step of introducing the sheath into the abdominal cavity is performed using an applicator capable of being introduced into the patient and deploying a sheath once within the abdominal cavity.

20. A method according to claim 12, wherein the insufflation of step b) is reduced before the undissected appendix is removed through the one or more incisions in step h).

* * * * *